United States Patent [19]
Morford et al.

[11] Patent Number: 5,985,063
[45] Date of Patent: Nov. 16, 1999

[54] METHOD FOR PRESERVATION OF HOP PLANTS AND HOP PLANT MATERIAL

[76] Inventors: Bruce Morford; Melaine Morford, both of 40 Island Rd., White Swan, Wash. 98952

[21] Appl. No.: 09/138,148

[22] Filed: Aug. 21, 1998

Related U.S. Application Data

[62] Division of application No. 08/563,931, Nov. 29, 1995, Pat. No. 5,798,150.

[51] Int. Cl.$^6$ ............................................. A01N 3/00
[52] U.S. Cl. .................................. 156/57; 427/4; 428/17; 428/22; 428/24
[58] Field of Search ................................. 156/57; 427/4; 428/17, 22, 24

[56] References Cited

U.S. PATENT DOCUMENTS

| | | | |
|---|---|---|---|
| 3,895,140 | 7/1975 | Sheldon et al. | 428/22 |
| 4,243,693 | 1/1981 | Nordh | 427/4 |
| 4,287,222 | 9/1981 | Robinson | 428/22 X |
| 4,328,256 | 5/1982 | Romero-Sierra et al. | 428/22 X |
| 4,710,394 | 12/1987 | Sellegaard | 427/4 |
| 4,808,447 | 2/1989 | Baker | 428/17 |
| 4,828,890 | 5/1989 | Tiedeman et al. | 427/4 X |
| 4,980,194 | 12/1990 | Allison et al. | 427/4 |
| 5,399,392 | 3/1995 | Sellegaard | 428/24 |
| 5,798,150 | 8/1998 | Morford et al. | 156/57 X |

*Primary Examiner*—Henry F. Epstein
*Attorney, Agent, or Firm*—Stratton Ballew PLLC

[57] ABSTRACT

A plant material is preserved by immersing a cross sectional surface of a severed stem, stalk, trunk or vine of a plant material into a preservative solution. The preservative solution can include a suitable dye. The plant material remains intertwined with its trellis, lattice or similar support during a preservation process. Alternatively, the plant material remains in a natural configuration during the preservation process. Also alternatively, the plant material also remains in a natural orientation during the preservation process. The cut stem, stalk, trunk or vine can be immersed in a container of preservative solution, at or near the time the stem, stalk, trunk or vine is severed. The cut stem stalk, trunk or vine of the plant can also be tied to a container of preservative solution. A rain shroud can also be placed over the container of preservative solution that contains the severed stem, stalk, trunk or vine of the severed plant, to protect the preservative solution during the preservation process. The rain shroud prevents the dilution of the preservative and the dyes by rain and the fouling of the solution by dust and debris. The preserved plant material can be a vine, including leaves, stalk, stem, flowers, cones, seeds and/or fruit. A preserved plant material can also be a hop plant, or portions of a hop plant, of the genus and species *Humulus lupulus*.

13 Claims, No Drawings

METHOD FOR PRESERVATION OF HOP PLANTS AND HOP PLANT MATERIAL

This application is a divisional of application Ser. No. 8/563,931 filed Nov. 29, 1995 (pending).

TECHNICAL FIELD

This invention relates to preserving hop plants and plant material. More particularly, the method can also be employed for the preservation of plant material, including hop plants for ornamental purposes.

BACKGROUND OF THE INVENTION

The preservation and dying of plant material is a well known process. Because simply drying plant material leaves it brittle and easily destroyed, a preservation process is often used to render the plant more durable for use in decorative arrangements. Often, dyes are also added to enhance or replace the natural color of the plant material for aesthetic reasons.

One known method for preserving plant material involves the use of the plant's own water and nutrient transport system, the xylem. The xylem transports water and dissolved minerals throughout the plant while it is growing, and for a time after the plant is severed from its root system. Once a plant has been severed from its root system, a preservative solution can be introduced by simply exposing the cut xylem to a preservative solution. The preservation solution then replaces the fluids which were supplied to the xylem by the root system. The preservative solution can contain a variety of components selected to preserve the plant's tissues. This known preservation method results in the systemic replacement of the plant material's natural internal fluids with a preservative solution. The preservative solution can also include the coloring of the plant material by adding a dye to the preservative solution.

Several problems arise when preserving plant material using this known method. The plants which are to be preserved and/or dyed must be harvested and transported to a processing location, often resulting in damage to the stem, trunk, stalk or vine of the plant. Moving a plant, especially a vine plant, causes trauma to that plant. Moving a plant can change the configuration of the plant. A plant's configuration is the spatial relationship between its individual branches and vines. Changing the configuration of the plant results in the crimping, kinking or damage to plant tissues. This damage impedes the uptake of preservatives and/or dye solutions.

"Uptake" is a term referring to the infusion of a preservative solution into a plant. "Uptake" is a relative term, without specific units of measure. A plant "uptakes" a solution, meaning the plant pulls the solution from a container into the tissues of the plant.

The orientation of each part of a plant, including leaves and flowers, is naturally controlled by the plant in response to its environment. This environment includes neighboring plants and leaves, sun and shade. Changing the orientation of the plant causes trauma to the plant, and significantly reduces the xylem's efficiency in transporting fluid through the plant.

At a minimum, the careful transport of larger plants to a processing facility for treatment is awkward and time consuming. Transport also results in trauma to the plant due to the change in orientation of the plant which slows the uptake of preservative solution. More importantly, transport results in changes in the plant's configuration which impedes the uptake of preservative solution.

Prior methods fail to address the support of the plant material to be preserved to maintain the configuration and orientation of the plant to facilitate the preservation process. The U.S. Pat. No. 4,828,890 to Tiedeman et al., teaches only the preservation of self supporting plants and shrubs, such as palms and baby's breath. For the varieties listed in Tiedeman et al. '890, the support of the plant material is not critical to the preservation process. A method is needed that enables the preservation of larger vines, trees and shrubs that require support to facilitate and enhance the preservation process.

There are situations where damage to the plants' internal structures impedes the uptake of preservative solutions. One method currently used in those situations has been to apply these solutions directly to the plant tissues. This requires large quantities of solution sufficient enough to totally immerse the plant or plant segments, resulting in added expense and waste. Another current method has been to cut the plant material into segments, or only preserve smaller cuttings, flowers or branches.

These methods increase the number of sites for absorbing the preservative solution, and minimize the distance preserving and coloring solutions must travel through tissues. However, larger displays of preserved plants require intact and entire plants. These prior methods cannot supply plant material for this demand. These prior methods also use more labor to accomplish this unsatisfactory result.

The preservation of hop plants presents particular challenges due to the unwieldy size and shape of the plant. The hop plant, *Humulus lupulus*, grows on a network of trellises, lattice works, poles, strings and wires which are employed for support. Hop plants typically attain heights of eighteen to twenty feet. The vertically winding stems of hop plants are generally referred to as bines in the hop growing industry. The predominantly horizontal branches from the main bines are referred to as laterals. The female hop cone is at present commercially desirable solely for its lupulin and essential oils, which are used as a flavoring in beer. Hops, an integral ingredient in beer, provide flavor and act as a bacteriostat. Bacteriostats inhibit the growth of undesirable bacteria and mold. Hop plants and have not been preserved for ornamental purposes.

From the foregoing, it can be seen that a need exists for a method that preserves plant material without first injuring the plant material during harvest and transport of the plant material to a processing location.

A related need exists for a method that includes the introduction of a preservative solution into a plant, severed from its root system, performed in a manner that maximizes the uptake of the preservative solution.

A related need exists for a preserved hop plant.

A need also exists for a dye to be added to the preservative solution for the preservation and dyeing of the hop plants and plant material.

SUMMARY OF THE INVENTION

According to the invention, plant material is preserved by immersing a cross sectional surface of a severed stem, stalk, trunk or vine of a plant material into a preservative solution.

According to an aspect of the invention, the preservative solution can include a suitable dye.

According to another aspect of the invention, the plant material remains intertwined with its trellis, lattice or similar support during a preservation process.

According to a related aspect of the invention, the plant material remains in a natural configuration during the preservation process.

According to another related aspect of the invention, the plant material remains in a natural orientation during the preservation process.

According to another aspect of the invention, the cut stem, stalk, trunk or vine is immersed in a container of preservative solution, at or near the time the stem, stalk, trunk or vine is severed.

According to a related aspect of the invention, the cut stem stalk, trunk or vine of the plant is tied to a container of preservative solution.

According to yet another aspect of the invention, a rain shroud is placed over the container of preservative solution that contains the severed stem, stalk, trunk or vine of the severed plant, to protect the preservative solution during the preservation process. The rain shroud prevents the dilution of the preservative and the dyes by rain and the contaminating of the solution by dust and debris.

According to another aspect of the invention portions of hop plants are preserved. According to another aspect of the invention, the plant material is a vine, including leaves, stalk, stem, flowers, cones, seeds and/or fruit.

According to still another aspect of the invention, the plant material is a hop plant of the genus and species *Humulus lupulus*.

According to another aspect of the invention, a portion of a hop plant is preserved.

According to a related aspect of the invention, the portion of a hop plant is also dyed.

DESCRIPTION OF SPECIFIC EMBODIMENTS

The preservation of a plant comprises several steps. First, a living, growing plant is selected from the tracheophyte group (vascular plants). Vascular plants use xylem tissues to transport water and minerals through the plant. The term "plant" refers to an entire plant, or a portion of a plant, or plant material. In their development of a preservative process, the applicant determined that when the plant to be preserved was damaged in transport and handling, the uptake of preservative solution by the xylem was impeded. Damage to the xylem reduced or completely stopped the flow of preservative solution, rendering the preservation process ineffective.

When left unaltered in a natural configuration during the preservative process, the plant keeps its xylem intact and functional. The term "natural configuration" refers to the natural overall growing position of the plant. For example, the configuration of the plant grown on a trellis is maintained, by leaving the plant on the trellis. It is not kinked, re-oriented, twisted or bent. Horizontal portions of the plant remain horizontal. Vertical portions of the plant remain vertical. This avoids damage to the xylem tissues, which could result from attempting to remove the plant from its supports. Particular care should be taken to avoid injury to the xylem. Any crimps, bruises, kinks or cuts will reduce the effectiveness of the preservation and coloring process, and in the uptake of preservative solution.

The applicant also discovered that changing the plant's natural orientation slowed the preservation process. The term "natural orientation" refers to the natural growing position of individual elements of the plant, such as leaves and flowers. The plant orients each leaf and flower relative to neighboring leaves and flowers and also relative to environmental factors such as, sun and shade. Drastically altering the natural orientation of a plant causes trauma to the plant that slows transpiration, and so impedes the preservation process by preventing the preservation of the extremities, especially in larger vines and shrubs.

The applicant also found that any delay in placing the cut into solution also resulted in a poor uptake of the preservative solution by the plant, especially by the extremities of larger trees vines and shrubs. However, U.S. Pat. No. 4,243,693 to Nordh teaches the delay of up to one day after cutting, before immersion into a preservative solution. The purpose of this delay, according to Nordh '693, was to condition the plant to a narrow range of environmental conditions and also to temporarily wilt the plant. Nordh '693 teaches this temporary wilting to increase the osmotic pressure and hence the "sucking-up" of preservative solution when the plant is placed into it.

The applicant determined that Nordh '693 teaches away from a more effective technique. Delays in placing the cut plant into preservative solution resulted in the plant exhibiting a wilt as it went into shock. Also, air bubbles, or air embolisms, formed in the xylem tissues near the point where the plant was cut. An embolism of air blocks the efficient transfer of fluids into the plant. The cohesive strength of water helps draw it through the small xylem tubes, replacing water being transpired from the leaves. If an air bubble forms in the xylem, the water's surface tension breaks, the xylem becomes effectively blocked and water transport stops. While a slight delay does not result in a total blockage, it results in a slowing of the uptake of the preservative solution. Such a delay reduces the uptake of solution and prevents the preservation of the plant's extremities.

In contradiction to Nordh '693, the present method requires placement of the severed stem, stalk, trunk or vine promptly into a preservative solution at or near a time that the plant is severed from its root system. As used herein, the term "near a time" is a length of time from when the plant is severed from its root system, up until, but prior to the wilting of the plant or the formation of an air embolism. Wilting as an outward sign of shock indicates a reduction in xylem efficiency. Further, the formation of air embolisms significantly impede the xylem's function.

This length of time for placement into preservative solution depends upon how rapidly the plant's vascular system pulls liquid up the tissues of the xylem. For a large hop plant a delay greater than ten minutes likely results in an incomplete uptake of the preservative solution. Preferably, the severed and completely exposed cross sectional area of the plant should be immersed in the preservative solution in less than one minute, more preferably in less than five seconds, and ideally in under two seconds. Less active plants do not require such quick immersion, especially if the ambient temperature is low.

When the plant's stem, stalk, trunk or vine is cut from the root system, the cut should be made at the base of the plant, as close to the ground as practicable. The root system begins to branch out from the plant at a root crown. The root crown is located proximate to the base of the plant. Preferably the cut should be made no more than ten centimeters above the root crown, but the point defined as the root crown is the more preferred point to make the cut.

The preservative solution includes ingredients that are typically employed for the systemic preservation of plant materials. For example, the preservative solution can include water to which a quantity of glycerine is added. The glycerine should be of a near technical grade, visually clear and free from odor and suspended impurities.

Deionized water is preferred, as anions present in tap water can also impede the uptake of solution by the plant. A surfactant can be added to the water for deionization.

The preservative solution can be a dilute solution, with only one part of glycerine for twenty parts water, but preferably, the solution should be at least glycerine and water an ratio of 1:10. A stronger glycerine solution is preferred, with an approximate glycerine to water ratio of up to 1:2 by volume. Most preferably a glycerine to water ratio of 1:4 is used.

The applicant prefers to mix larger quantities of preservative solution, reducing labor and minimizing measuring errors encountered in the mixing of multiple small quantities. A 280 gallon batch of solution is preferably distributed into multiple containers for individually preserved plants. A preferred container is a plastic pot. A pot will preferably hold up to five gallons of solution when the applicant preserves and colors hops plants.

Potassium sorbate (CAS #590-00-1) can be added to the preservative solution as a bacteriostat. The addition of approximately 1 to 10 pounds of potassium sorbate per 280 gallons of solution prevents the degradation of the preserved tissues. More preferably, 2.5 pounds of potassium sorbate per 280 gallons of solution prevents the degradation of the preserved tissues for an extended period. Preserved hop plants stored or displayed in low humidity environments may last indefinitely, but a period of up to two years is expected under normal storage and display conditions. Other inhibitors, besides potassium sorbate, are also known in the industry and can be substituted with equal effectiveness.

Citric acid (CAS #77-92-9), preferably in granulated form for ease of handling and measuring, is preferably added to the solution for its antioxidant properties, and to lower the pH of the preservative solution. The pH of the preservative solution should be adjusted to approximately pH 4, but should always be in the range between pH 3.5 and pH 7.5.

A dye may be added to the preservative solution to achieve a colored product. The color selected may either impart a natural color for the preserved plant material, or an unnatural color chosen for visual impact. The dye can be chosen from a variety of commercially available plant and floral product systemic dyes. Robert Koch Industries, Inc. of Bennett, Colo., Design Master of Boulder, Colo. and Keystone Dye of Santa Fe Springs, Calif., supply systemic acid dyes that perform adequately. The amount of the dye added to the preservative solution may be varied dramatically to achieve the desired effect. Each plant variety will take up the dye with different results; a small scale trial will help determine the concentration of dye needed to achieve the desired result.

To prevent a gust of wind from lifting the bine, stalk, stem, trunk or vine from lifting out of the container of preservative solution, the bine, stalk, stem, trunk or vine can be tied to the container. The applicant wraps short length of a strong cord or twine around the stalk, stem, trunk or vine and then attaches the cord or twine to the container of preservative solution.

When necessary, a shroud may be wrapped around the severed trunk, stem or vine at its base, covering the container of the preservative solution to prevent dilution or contamination of the solution during the preservation process by rain showers or other precipitation. The shroud also prevents loss of the solution by evaporation. The shroud helps to maintain a consistent preservation solution and prevents the fouling of the xylem tissues due to a contaminated preservation solution.

The length of time the exposed cut of the stem, trunk or vine should be immersed in the preservative solution will depend on several factors. Ambient temperature and humidity are important variables, as are the characteristics of the plant species and each plant's transpiration rate. A simple way to monitor the uptake of the preservative solution by the plant is to track the level of solution in the preservative solution container. When the level of solution remains constant for a period of time, or the plant uptakes all of the solution placed into the container, the process is complete. If the extremities of the plant do not appear preserved or dyed, but the solution is no longer being taken up by the plant, the only way to achieve the preservation of these extremities is to cut them from the plant and totally immerse them into the preservative and/or dye solution.

At the completion of uptake, the plant remains in place for a drying period. This period can be for as long as three weeks, but for hop plants it is preferably between five days and one week. The moisture content for a hop plant at the end of the drying period should be between 8% and 10%, by weight. After the drying period, the plant can be removed from its supports in any conventional manner. The preserved and colored product is ready for storage, packaging or shipping. The preservative solution effectively permeated glycerine, antioxidants and bacteria inhibitors throughout the plant. The plant remains supple, resilient, and resistant to decomposition, especially in low humidity environments. If a dye is used, the dyed color is also retained indefinitely.

Hop plants preserve especially well by this process. While preserved hop plants have not been previously preserved for ornamental, they possess unusual and beautiful foliage. Preserved hop plants, including bines, laterals, leaves and cones, would provide a unique and decorative arrangement in any situation where a distinctive and appealing preserved ornamental plant is desired. Hop plants also accept dyes with remarkable effect, resulting in a decorative product with high ornamental value. Keeping the hop plant intact on the support on which it has grown, thus leaving the hop bines and laterals in their natural configuration, allows efficient uptake of the preservative. The entire preservation process often occurs in less than 48 hours, depending upon the rate the plant uptakes the preservative solution. The speed and efficiency of the hop plant in absorbing the preservative solution and transferring it through its active xylem to all of the plant's extremities is an unexpected and extraordinary discovery.

Especially for hops, it was discovered that timing plays a vital part in the effective preservation of the plant. Not only must the cut bine immediately contact the preservative solution at the root crown cut, but the time of day is also critical. The water transport and transpiration of the hop plant slows to a minimal level during the hot hours of the day. In the early evening as the ambient temperature drops, the plant again becomes active. This is the optimal time to cut the plant as close to the ground as possible, and immediately immerse the xylem of the severed plant into the preservative solution. Again, this solution can contain a dye for imparting a color as desired to the preserved plant. The concentration of the dye in the preservative solution is subjective. The addition of 32 ounces of a systemic concentrate dye in a 280-gallon container has been used with success to achieve a vibrant hue, but dye amounts ranging between 4 ounces to 8 pounds per 280-gallon container are also used.

The total amount of preservative solution placed in the pot for the individual plant will vary with the expected uptake of the plant. A typical hop plant requires approximately 1.5 gallons of solution. Larger hop plants can require up to 4 gallons of solution, while smaller plant may only require a half of a pint of solution.

Hop plants preserved by drying or by dipping or spraying them with a preservative coating do not possess the ornamental properties of a systemically preserved hop plant as described above. A systemically preserved hop plant is almost indistinguishable in scent and appearance from a fresh hop plant. This is especially true when green dye is supplemented into the preservative solution.

A hop plant can be systemically preserved by placing segments of a hop plant into a container of preservative solution. A dye can also be added to the container of preservative solution to achieve a preserved and dyed floral product.

Although a preferred embodiment of the invention has been illustrated and described, various alternatives, modifications and equivalents may be used. A portable or mobile trellis system for plants is one alternative, which would allow the plants to be cut close to the ground, as described above, but otherwise left intact on the mobile trellis. The trellis, with plants still suspended thereon, can then be moved to a nearby processing location for treatment with the preservative solution. Such a mobile trellis structure would afford better control of the environment where the preservation takes place, avoiding storms and temperature extremes. Moving the plant with its supports to a processing location or moving the plant intact on this mobile support, can be achieved while maintaining the natural configuration and closely maintaining the natural orientation of the plant.

Another alternative includes the erection of a support system for a plant, enabling it to then be severed and undergo the preservation process without changing the plant's natural configuration, also preserving the natural orientation of the plant as much as practicable. Supports could include trellises, props, cranes or wires. Plants such as vines generally, grapes, trees, shrubs and ornamental foliage could be processed with the aid of a support. The plant would be attached to the support then severed from its root system, thereby suspended from the support. Such a support could also be temporary, used only during the preservation process.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principles of the invention, and the disclosure is not intended to limit the invention to the particular embodiments described. Those with ordinary skill in the art will appreciate that other embodiments and variations of the invention are possible which employ the same inventive concepts as described above. Therefore, the invention is not to be limited except by the following claims, as appropriately interpreted in accordance with the doctrine of equivalents.

What is claimed is:

1. A method for preserving a hop plant material for use as a floral product comprising the steps of:
   a. selecting a living, hop plant material, said hop plant material having a root system;
   b. severing the hop plant material from the root system; and
   c. exposing the hop plant material to a glycerine containing preservative solution, so that said plant material uptakes said preservative solution.

2. The method of claim 1, further comprising the step of
   d. dying the hop plant material.

3. A method for preserving a hop plant material for use as a floral product comprising the steps of:
   a. selecting a living, hop plant material having a root crown;
   b. severing the hop plant material proximately to the root crown of said hop plant material, to completely expose a cross sectional surface; and
   c. exposing the cross sectional surface of the hop plant material to a glycerine containing preservative solution substantially, so that said plant material uptakes said preservative solution.

4. The method of claim 3, further comprising the step of
   d. dying the hop plant material.

5. A method for preserving a plant material for use as a floral product comprising the steps of:
   a. selecting a living, hop plant material;
   b. supporting the selected hop plant material, to maintain said hop plant material in a natural configuration;
   c. severing the hop plant material from a root system of said hop plant material, completely exposing a cross sectional surface of a stem, a stalk, a trunk or a vine; and
   d. exposing the cross sectional surface of the hop plant material to a glycerine containing preservative solution while said plant material is maintained in the natural configuration, so that said plant material uptakes said preservative solution.

6. The method of claim 5, wherein the step of supporting the selected hop plant material includes maintaining said selected hop plant in a natural orientation, and the step of exposing the cross sectional surface of the hop plant material includes maintaining said hop plant material in the natural orientation.

7. The method of claim 5, wherein
   the step of severing the hop plant material includes severing the hop plant material proximate to a root crown of the hop plant material.

8. The method of claim 5, wherein the step of exposing the cross sectional surface of the plant material to the preservative solution includes dying the plant material by exposing said cross sectional surface to a dye that uptakes into said plant material with said preservative solution.

9. The method of claim 5, wherein the step of exposing the cross sectional surface of the severed plant material includes immersing said plant material in the preservative solution substantially at or near a time that said plant material is severed from the root system.

10. The method of claim 5, with the additional step of:
    e. covering a container of the preservative solution to prevent evaporation, dilution and fouling of said preservative solution during the preservation process.

11. The method of claim 5, with the additional step of:
    e. removably attaching the severed plant material to a container of the preservative solution.

12. The method of claim 5, wherein the step of severing the selected plant material includes severing said plant material substantially proximate a base of the plant.

13. The method of claim 5, with the additional step of:
    e. drying the plant material substantially in place for a drying period.

* * * * *